US005565195A

United States Patent [19]

Bélanger et al.

[11] Patent Number: 5,565,195
[45] Date of Patent: Oct. 15, 1996

[54] *SPOROTHRIX FLOCCULOSA* ATCC 74320 AND COMPOSITIONS THEREOF WITH DODEMORPH-ACETATE

[75] Inventors: Richard R. Bélanger; Mohammed Benyagoub, both of Ste-Foy, Canada

[73] Assignee: Universite Laval, Quebec, Canada

[21] Appl. No.: 375,794

[22] Filed: Jan. 20, 1995

[51] Int. Cl.[6] .......... A01N 63/04; C12N 1/14; C08B 3/06

[52] U.S. Cl. .......... 424/93.5; 435/254.1; 435/911; 504/117; 536/69

[58] Field of Search .......... 424/93.5; 435/254.1; 504/117; 536/69

[56] References Cited

U.S. PATENT DOCUMENTS 4,751,082 6/1988 Schaerffenberg .......... 424/93.1

OTHER PUBLICATIONS

Batra, S. W. T., 1982, *Science,* 215:134–139.
Bélanger, R. R. et al., 1994, *Plant Disease,* 78(4):420–424.
Hajlaoui, M. R. et al., 1991, *Neth. J. Plant Pathol.,* 97:203–208.

Hijwegen, T., 1986, *Neth. J. Plant Pathol.,* 92:93–95.

Hijwegen, T., and H. Buchenaeur, 1984, *Neth. J. Plant Pathol.,* 90:79–84.

Jarvis, W. R. et al., 1989, *Mycol. Res.,* 92:162–165.

Klecan, A. L. et al., 1990, *Phytopathol.,* 80:325–331.

Mukerji, K. G., and Garg, K. L., 1988, *Biocontrol of Plant Disease,* vol. I., CRC Press, Boca Raton, Florida.

Payne, C. C., 1988, *Phil. Trans. R. Soc. Lond. B,* 318:225–248.

Traquair, J. A. et al., 1988, *Can. J. Bot.,* 66:926–933.

Papavizas, G. C., 1983, *Phytopathology,* 73:407–411.

*Primary Examiner*—Michael G. Wityshyn
*Assistant Examiner*—L. Blaine Lankford
*Attorney, Agent, or Firm*—Klauber & Jackson

[57] ABSTRACT

The present invention relates to a new strain of *Sporothrix flocculosa* Atcc 74320 resistant to the fungicide dodemorph-acetate and its use as a biofungicide in integrated pest management with the fungicide.

6 Claims, 3 Drawing Sheets

*SPOROTHRIX FLOCCULOSA* ATCC 74320 AND COMPOSITIONS THEREOF WITH DODEMORPH-ACETATE

BACKGROUND OF THE INVENTION (a) Field of the Invention

The invention relates to the development of a new strain of *Sporothrix flocculosa* resistant to the fungicide dodemorph-acetate and its use as a biofungicide in integrated pest management.

(b) Description of Prior Art

Despite the development of various strategies of pest control (Batra, S. W. T., 1982, Science, 215:134–139), the use of synthetic chemical pesticides have predominated since 1950. However, the adverse environmental consequences in using certain toxic chemical pesticides, the development of resistance by certain pests to chemical pesticides and the increasing production costs for new compounds are currently encouraging greater interest in biological control agents (Mukerji, K. G., and Garg, K. L., 1988, Biocontrol of Plant Disease, Vol. I., CRC Press, Boca Raton, Fla.; Payne, C. C., 1988, Phil. Trans. R. Soc. Lond. B, 318:225–248).

Powdery mildew fungi are important plant diseases for which the control relies heavily on fungicides. This trend could be modified in light of the discovery of a number of hyperparasites and antagonists against these fungi (Hijwegen, T., and H. Buchenaeur, 1984, *Neth. J. Plant Pathol.*, 90:79–84). For instance, Tilletiopsis Berx species have been found to control Erysiphe graminis DC var. hordei Em. March. (Klecan, A. L. et al., 1990, Phytopathol., 80:325–331), *Sphaerotheca fuliginea* (Schlecht.:Fr.) Poll. (Hijwegen, T., 1986, Neth. J. Plant Pathol., 92:93–95), as well as other powdery mildews (Hijwegen and Buchenauer, 1984, idem). In addition, recent studies have shown that a yeast like fungus, *Sporothrix flocculosa* (Traquair, Shaw & Jarvis; Traquair, J.A. et al., 1988, *Can. J. Bot.*, 66:926–933) antagonized the powdery mildew pathogen of cucumber (Jarvis, W.R. et al., 1989, *Mycol. Res.*, 92:162–165) and rose (Hajlaoui, M.R. et al., 1991, *Neth. J. Plant Pathol.*, 97:203–208). When applied at the rate of $1\times10^6$ spores/ml under controlled conditions, *Sp. flocculosa* reduced powdery mildew colonies on leaves of rose within a 48-hour period (Hajlaoui and Bélanger, 1991, idem). When used under commercial conditions, *Sp. flocculosa* proved as effective as fungicides at controlling rose powder mildew (Bélanger, R. R. et al., 1994, *Plant Disease,* 78(4):420–424).

One of the major constraints in the use of a biofungicide is its own susceptibility to fungicides currently used in the crops to protect them (Papavizas, G. C., 1983, *Phytopathology,* 73:407–411). With the current scheme of integrated control of plant diseases, the combination or alternance of natural and chemical fungicides is a very appealing strategy to optimize both disease control and protection of the environment. However, this approach presupposes that the biocontrol agent is resistant to the fungicide used for the particular disease to control. Therefore, development of a *Sp. flocculosa* strain resistant to fungicides used in the control of powdery mildew would allow the integrated use of biological and chemical approaches in a disease management scheme.

It would be highly desirable to be provided with a strain of *Sp. flocculosa* resistant to important fungicides registered for the control of powdery mildew.

SUMMARY OF THE INVENTION

The aim of the present invention is to provide for a new *Sp. flocculosa* strain, resistant to the fungicide dodemorph-acetate, a sterol biosynthesis inhibitor used for powdery mildew control, and which can be used as a biofungicide effective against powdery mildew in with or without a mixture of natural and chemical fungicides in an integrated control of plant diseases.

In accordance with the present invention there is provided a new strain of *Sporothrix flocculosa* resistant to the fungicide dodemorph-acetate and its use as a biofungicide in integrated pest management.

DETAILED DESCRIPTION OF THE INVENTION

Figure 1A:
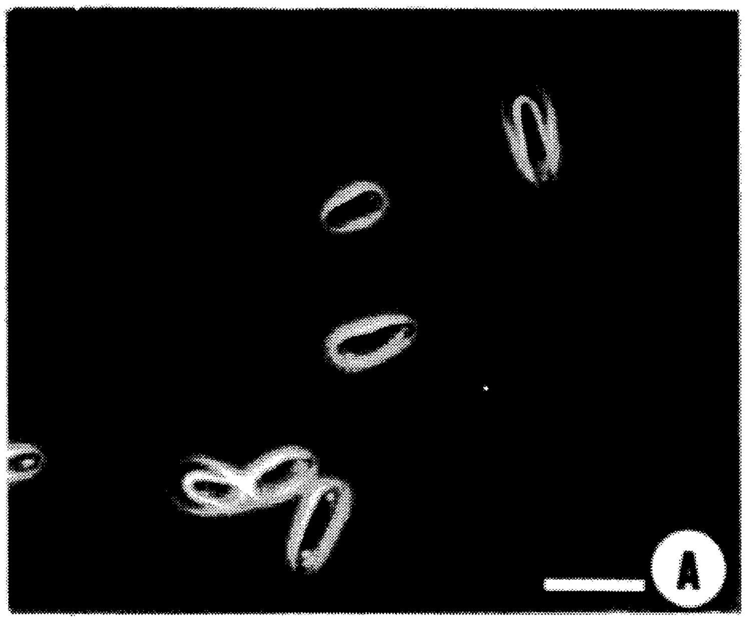
FIG. 1 is a picture of the resistant strain (SF-$R_M$; Right) and of a wild type (Left) growing in a dodemorph-acetate corrected medium.

Development of a dodemorph-acetate resistant *Sp. flocculosa* strain

Several isolates of the mildew biocontrol fungus *Sporothrix flocculosa* were screened for their resistance to the systemic fungicide dodemorph-acetate (MELTATOX™) by repeated exposure to increasing concentrations of the fungicide. Through this procedure, a new strain which is able to grow and form colonies on solid media amended with 300 μg/ml of fungicide was obtained. This resistance trait was maintained following several subcultures on fungicide-free media. When tested for its biocontrol ability, the dodemorph-resistant strain was able to colonize conidia and mycelium of *Sphaerotheca fuliginea* as efficiently as the wild strain. In addition, the new strain was not hampered in its properties to control powdery mildew when applied in mixture with dodemorph-acetate while the wild strain was unable to colonize the pathogen in presence of the fungicide. This is the first report of a fungus resistant against dodemorph-acetate for a powdery mildew biocontrol agent. This new strain of *Sporothrix flocculosa* could find practical application in integrated control of powdery mildew, especially on roses.

Microorganisms

Single-spore isolates of *Sporothrix flocculosa* (SF-1) were obtained by reisolating the fungus from rose leaves that were submitted to weekly applications of a fungal suspension initiated from an isolate of S. flocculosa graciously provided by Dr. W.R. Jarvis, Harrow Research Station, Agriculture Canada. Stock cultures of the isolates were maintained at 4° C. on yeast-malt-peptone-dextrose agar (YMPDA) before being transferred in shake cultures at room temperature in liquid YMPD.

Mildewed cucumber (*Cucumis sativus* L.) cv. Corona leaf disks of 20 mm were cut from fully expanded leaves grown in a glasshouse. The leaf disks were selected so that approximately 90% of the area was covered by mycelium and conidia of *Sphaerotheca fuliginea* (Schlecten:Fr.) Pollacci.

Fungicide

Dodemorph-acetate (MELTATOX™, 400 g/L active ingredient (a.i.), BASF, Canada Inc.) was obtained from Plant Prod Québec (Laval, Québec). This fungicide was available as an emulsion and was added directly to the liquid culture media under concentrations specified below. The recommended dosage for rose powdery mildew control is 200 μg/ml.

Isolation of resistant mutants

The occurrence of resistant biotypes was screened by successive subcultures of tested isolates in liquid suspension containing increasing concentrations of dodemorph-acetate. Every 5 days, 2 ml of the culture suspension were transferred to fresh YMPD broth amended with a higher fungicide concentration. The adaptation was initiated with a dose of 40 μg dodemorph-acetate/ml that was increased gradually to 60, 80, 100 125, 150, 175, 200 and up to a concentration of 250 μg a.i/ml. At the end of the adaptation process, fungal propagules that had survived to the treatment were maintained on YMPD agar.

Exposure of different wild isolates of *Sporothrix flocculosa* to dodemorph-acetate inhibited strongly the development of fungal propagules even at low concentrations (40 μg/ml). Survival rate was low and most isolates could not be recovered following the initial culture in the fungicide-amended medium. The few isolates that were still showing growth at the lowest concentration were allowed further adaptation at 40 μg/ml before being transferred to media containing 60 μg/ml. Through this procedure, other isolates were lost at one stage or another of the adaptation process. However, after 53 transfers, we were able to obtain one fungal colony from one isolate that displayed sustained growth in a medium amended with a concentration of 250 μg/ml a.i. dodemorph-acetate, a dosage 25% superior to the recommended one. This colony was designated as a new strain and referred to as SF-$R_M$.

The preferred *Sporothrix flocculosa* strain SF-Rm of the present invention, has been deposited at the American Type Culture Collection (ATCC, 12301 Parklawn Drive, Rockville, Md. 20852 USA) on Dec. 21, 1994 under ATCC deposit number 74320. This deposit is available to be public upon the grant of a patent to the assignee, Université Laval, disclosing same. The deposit is also available as required by Foreign Patent laws in countries wherein counterpart applications are filed.

Figure 1B:
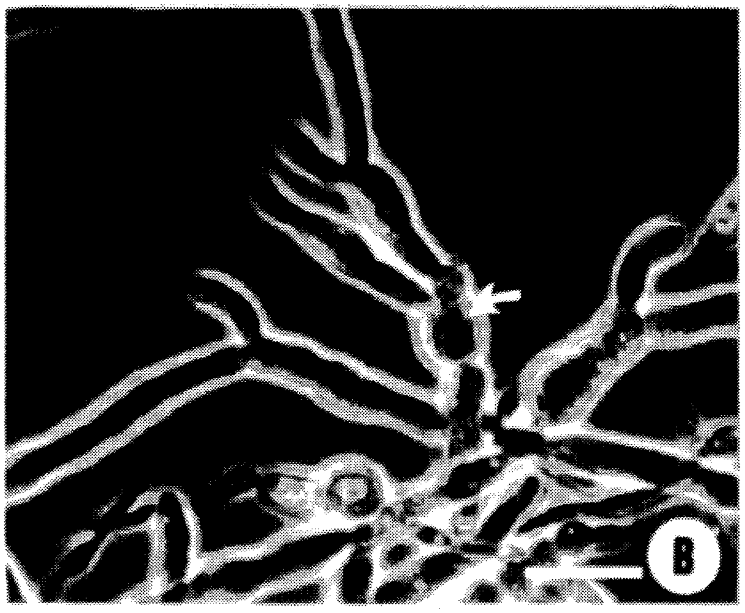

When grown in a liquid medium amended with dodemorph-acetate, strain SF-$R_M$ differed from the wild strain in morphological characteristics and sporulation (FIG. 1). These morphological differences were characterized by the formation of branched hyphae and chlamy-dospore-like structures (FIG. 1B).

Following ten transfers into fungicide-free YMPD broth, SF-$R_M$ exhibited the same level of resistance to dodemorph-acetate and the same growth characteristics.

The preferred concentration of dodemorph-acetate used in accordance with the present invention is about 0 to about 250 mg/ml of active ingredient.

Toxicity assays

In vitro fungitoxic activity of dodemorph-acetate was studied on YMPDA. Dodemorph-acetate was added to the autoclaved medium and mixed using a magnetic stirrer and dispensed (15 ml) into 9 cm Petri plates. Disks of seven day-old colonies from wild and resistant strains were plated on YMPD agar amended or not with dodemorph-acetate. Cultures were incubated at 24° C. and the colony radius was measured after 3, 8 and 14 days of incubation. Five replicate plates were prepared for each biotype and each fungicide concentrations tested (100 and 300 μg/ml). The experiment was repeated twice. The percentage of inhibition of radial growth of *Sp. flocculosa* was calculated as % Inhibition =[1-(treated/control)]×100.

The stability of the resistant strain was tested by reevaluating resistance after ten serial transfers into fungicide-free liquid YMPD.

In presence of dodemorph acetate at a concentration of 100 μg/ml, the wild strain (SF-1) was strongly inhibited in its development over time and at the end of the experimental period (14 days) percent growth inhibition had reached over 70%. When culture disks were inoculated on media plates containing 300 μg/ml of fungicide, SF-1 strain was completely inhibited.

With regards to the resistant strain, a small growth reduction was recorded within the first three days under both concentrations. In the following days, the percent of growth inhibition remained stable or was reduced, indicating that SF-$R_M$ strain had resumed a relative growth rate comparable to the control.

Biological properties

The resistant strains obtained from experiments described above were tested for their ability to control powdery mildew. Five leaf disks of mildewed cucumber were placed on moist filter paper in 9 cm Petri plates. The disks were sprayed lightly with one of the following suspensions: i) a cell suspension of *Sp. flocculosa* (SF-1) ($10^6$ cfu/ml) ii) a cell suspension of the putative resistant strain (SF-$R_M$) ($10^6$ cfu/ml), iii) a cell suspension of SF-1 in mixture with 100 or 300 μg/ml of dodemorph-acetate, and iv) a cell suspension of SF-$R_M$ in mixture with 100 or 300 μg/ml of dodemorph-acetate. The Petri plates were closed and sealed with parafilm and incubated at 24° C. in mixed fluorescent and incandescent light at 30 mE $m^{-2}$ $s^{-1}$ for 12-h photoperiod. Five leaf disks of mildewed cucumber were used for each treatment and the experiment was repeated twice.

The preferred concentration of *Sp. flocculosa* used in accordance with the present invention is about $1\times10^6$ spores/ml to about $1\times10^7$ spores/ml.

Effects of treatments on *S. fuliginea* was scored as an arbitrary scale described by Jarvis et al. (1989, *Mycol. Res.*, 92:162–165) where: 0=no colonization of powdery mildew, 1=1–20%, 2=11–40%, 3=31–60%, 4=51–70% and 5=81–100% dead colonies.

Figure 2:
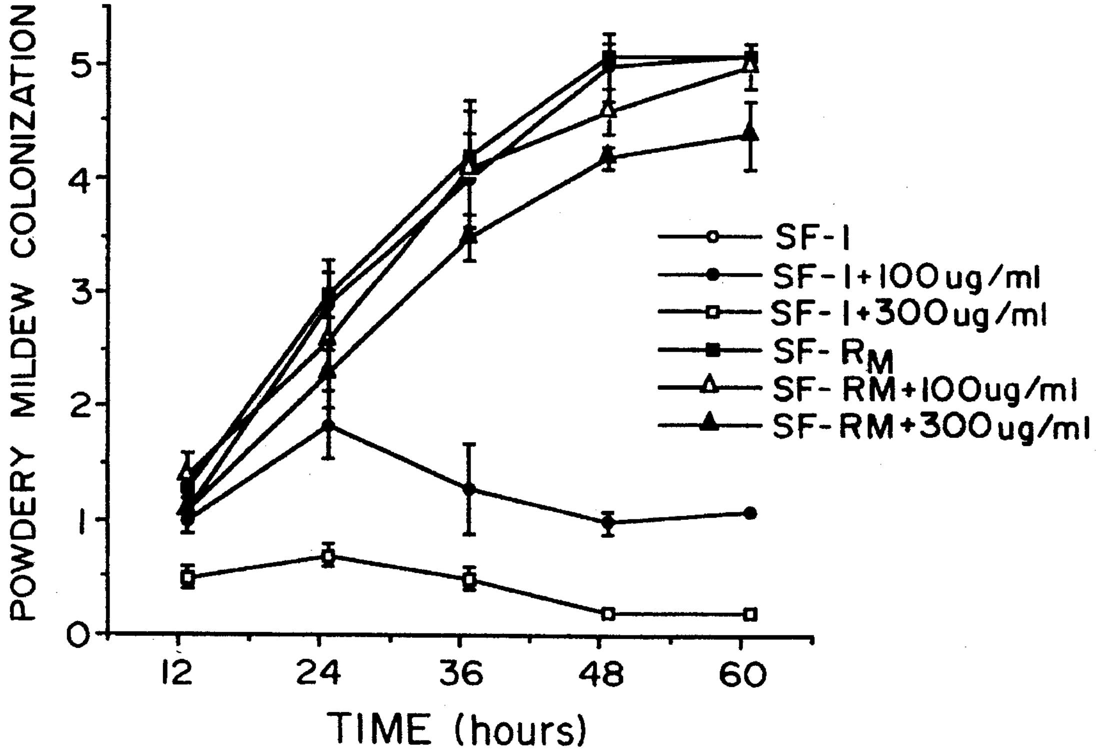
FIG. 2 is a graph of the colonization rate of the pathogen *Sphaerotheca fuliginea* by *Sporothrix flocculosa* (resistant and wild type strains) alone or in combination with dodemorph-acetate.

When tested for its ability at colonizing powdery mildew, resistant strain SF-$R_M$ displayed the same ability as the wild strain (FIG. 2.). It induced complete collapse of the conidia, conidiophores and hyphae of *S. fuliginea* within 48 h following application. In addition, strain SF-$R_M$ was just as effective at parasitizing *S. fuliginea* when applied in mixture with dodemorph-acetate (100 μg/ml). In fact, the colonization rate after treatment with SF-$R_M$+100 μg/ml was not significantly different from that after treatment with SF-1 or SF-$R_M$ alone (FIG. 2).

In mixture with 300 μg/ml of fungicide, a dosage 50% superior to the recommended concentration, the resistant strain displayed the same pattern of colonization as the wild strain and was only slightly delayed in its efficiency, namely after 48 h (FIG. 2). On the other hand, when the wild strain was applied in mixture with dodemorph-acetate it was unable to maintain its development in presence of the fungicide and its colonization of powdery mildew was extremely limited, especially in combination with 300 μg/ml of dodemorph acetate (FIG. 2).

Scanning electron microscopy

Leaf-disk samples of each treatment, plus treatment with distilled water, were collected after 48 hours and fixed with glutaraldehyde (3%, v/v) in 0.1M sodium cacodylate at pH 7.2 for 16 hours at 4° C., then rinsed three times with the same buffer, and postfixed by immersion with osmium tetroxide (1%, w/v) for 2 hours at 4° C. in sodium cacodylate buffer. The samples were dehydrated in series of ethanol solution graded in 20% steps. They were then mounted on aluminium studs and sputter-coated with gold to thickness of about 20 mm and examined with a Cambrige Stereoscan 5-150™ microscope at 20 Kv.

Figure 3A:
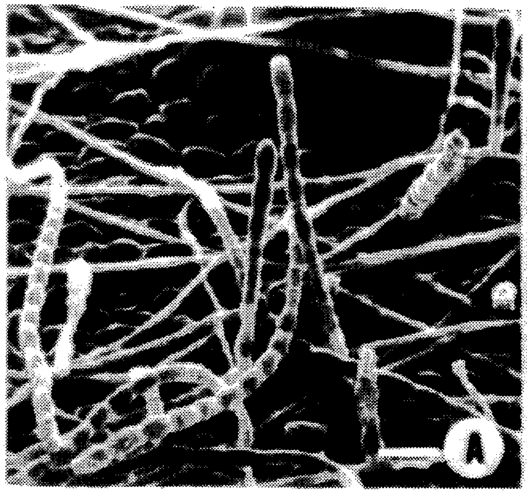
FIG. 3 is a composite picture of the development of *Sporothrix flocculosa* (resistant and wild type strains) alone or in combination with dodemorph-acetate.
Figure 3B:
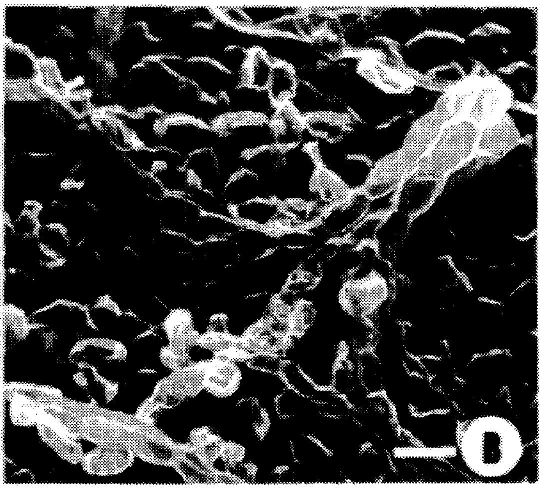
Figure 3C:
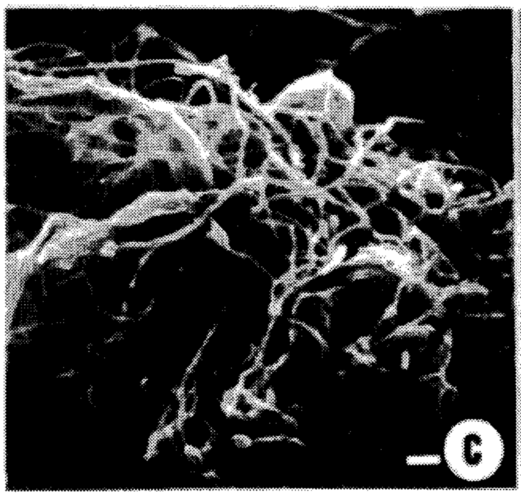
Figure 3D:
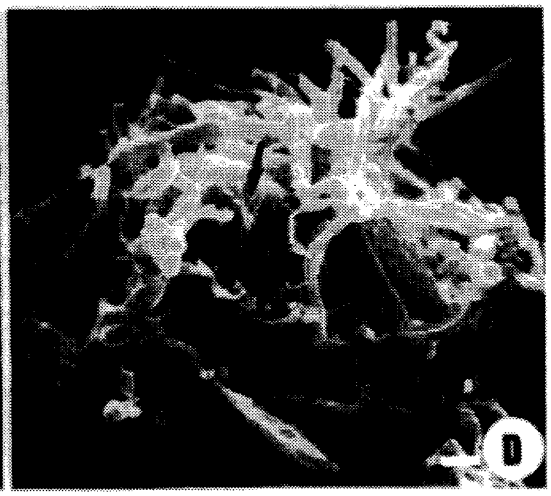
Figure 3E:
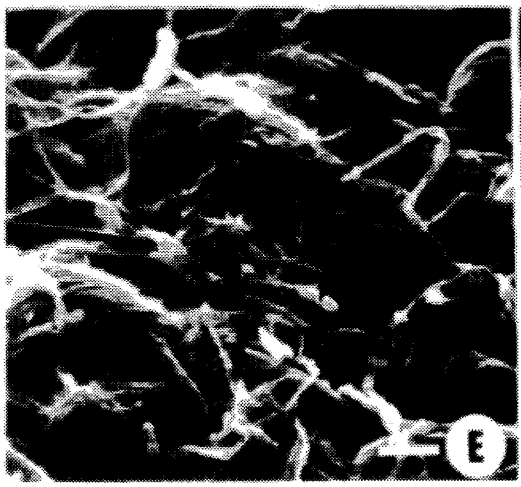
Figure 3F:
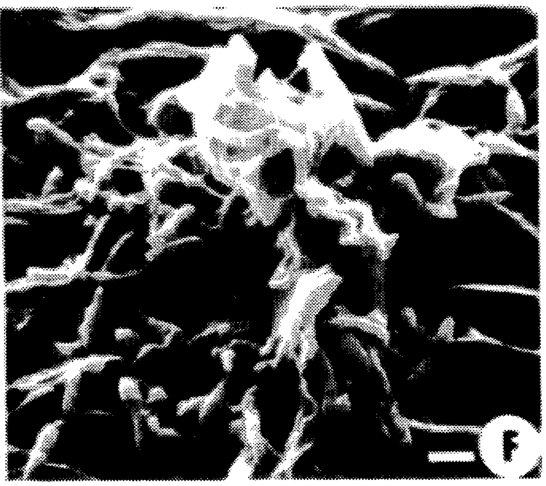

Scanning electron microscopy observations of powdery mildew colonies treated with water or dodemorph-acetate showed that fungicide treatment affected the hyphal integrity of the fungus, resulting in collapse of conidiophores and conidia (FIG. 3B). The colonies treated with water were turgid, with well-formed reproductive structures (FIG. 3A). When *S. fuliginea* was treated with inoculum of SF-$R_M$, the hyperparasite developed abundantly over the pathogen whether it was sprayed alone (FIG. 3C) or in mixture with the fungicide at 100 and 300 μg/ml (FIGS. 3D and 3F). By contrast, mixture of wild-strain of *S. flocculosa* with dodemorph-acetate resulted in death of the hyperparasite (FIG. 3E).

The results of the dodemorph-acetate resistant *Sp. flocculosa* strain of the present invention showed that SF-$R_M$ strain could colonize *S. fuliginea* as efficiently as the wild strain. Hyphae and conidia of *S. fuliginea* were collapsed and plasmolysed following colonization by SF-$R_M$ in a manner similar to the one reported in previous studies with *S. flocculosa*. This result suggests that the new biotype did not, lose its characteristics as a biocontrol agent.

Previous studies have shown that dodemorph-acetate and other morpholine fungicide can cause damage to plants. Indeed, dodemorph was shown to induce a drastic leakage of betacyanin from discs of beet roots and an efflux of electrolytes from discs of bean leaves and sections of barley leaves. Phytotoxity was also reported on rose plants treated with MELTATOX™ (dodemorph-acetate). Thus, the obtention of a dodemorph-resistant strain that possesses strong biocontrol ability may be useful for integrated pest management programs to maximize the effects of dodemorph-acetate on rose powdery mildew in greenhouses and to decrease the phytotoxity effects. In fact, with the combination of resistant-strain and fungicide, less chemical and fewer sprays may be required for adequate disease control in greenhouses at commercial-scale, and better disease control may be obtained than when either compound is used alone. In addition, the development of dodemorph-resistant strain of *Sp. flocculosa* with improved biocontrol characteristics may be a key to the practical use of this biocontrol agent in disease management.

In conclusion, the present invention pertains to the first report of resistance against the fungicide dodemorph-acetate by a fungus, in this case the powdery mildew antagonist *Sporothrix flocculosa*. This new strain of *Sp. flocculosa* (SF-$R_M$) was shown to have maintained its biocontrol properties and was just as effective at colonizing powdery mildew when used alone or in combination with dodemorph acetate. These results could lead to practical integrated control of powdery mildew diseases, especially on roses.

The present invention will be more readily understood by referring to the following example which is given to illustrate the invention rather than to limit its scope.

EXAMPLE I

Use of *Sporothrix flocculosa* strain SF-Rm as a biofungicide in combination or alternance with the fungicide dodemorph-acetate For the commercial control of rose powdery mildew, the formulated product of *Sporothrix flocculosa* (strain SF-Rm) can be used at the recommended concentration alone upon apparition of the first signs of the disease. If disease pressure increases, the product can be used in alternance with the fungicide dodemorph-acetate, or in combination by mixing it directly with the recommended or a lower concentration of the fungicide. When disease is kept in check again, one can resume using the biofiungicide alone or mix it with half the recommended concentration of fungicide.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A biologically pure culture of *Sporothrix flocculosa* ATCC 74320.

2. A method for the biocontrol of plant powdery mildew, which comprises administering to a plant a biofungicidal amount of a mixture containing *Sporothrix flocculosa* ATCC 74320 in the absence or presence of a fungicide in association with a biofungicidal carrier.

3. The method of claim 2, wherein said fungicide is dodemorph-acetate.

4. The method of claim 3, wherein said plant is a rose.

5. The method of claim 4, wherein the *Sp. flocculosa* is present in an amount of about $1\times10^6$ spores/ml to about $1\times10^7$ spores/ml.

6. The method of claim 5, wherein the dodemorph-acetate is in an amount of about 0 to about 250 mg/ml of active ingredient.

* * * * *